United States Patent [19]

Ward

[11] Patent Number: 4,458,679
[45] Date of Patent: Jul. 10, 1984

[54] COLD WEATHER RESPIRATORY MASK

[76] Inventor: Russell G. Ward, 2050 SW. 71st Ave., Portland, Oreg. 97225

[21] Appl. No.: 383,465

[22] Filed: Jun. 1, 1982

[51] Int. Cl.³ .................. A61M 15/00; A62B 7/00
[52] U.S. Cl. .................. 128/201.13; 128/205.25
[58] Field of Search .................. 128/201.13, 204.17, 128/206.12, 206.17, 205.25

[56] References Cited

U.S. PATENT DOCUMENTS

| | | | |
|---|---|---|---|
| 1,418,182 | 5/1922 | Tabor | 128/203.29 |
| 3,326,214 | 6/1967 | McCoy | 128/201.13 |
| 3,814,094 | 6/1974 | De Angelis et al. | 128/201.13 |
| 4,196,728 | 4/1980 | Granite | 128/201.13 |
| 4,200,094 | 4/1980 | Gedeon et al. | 128/201.13 |
| 4,325,365 | 4/1982 | Barbuto | 128/201.13 |

FOREIGN PATENT DOCUMENTS 1234531 2/1967 Fed. Rep. of Germany ................ 128/201.13

Primary Examiner—Henry J. Recla
Assistant Examiner—Karin M. Reichle
Attorney, Agent, or Firm—James D. Givnan, Jr.

[57] ABSTRACT

A mask for use in severe arid climates which includes a countercurrent exchange medium, confined within a mask shell, which salvages heat and moisture given off during exhalation for subsequent transfer to inhalation air. A shaped mask member forms the mask to fit snugly over the lower face and nose. A normally closed opening in the mask shell permits access to the mask interior and to the countercurrent exchange medium. Tubular inserts provide supplemental quantities of the medium as well, in a modified form, provide an interface for additional respiratory gear.

9 Claims, 6 Drawing Figures

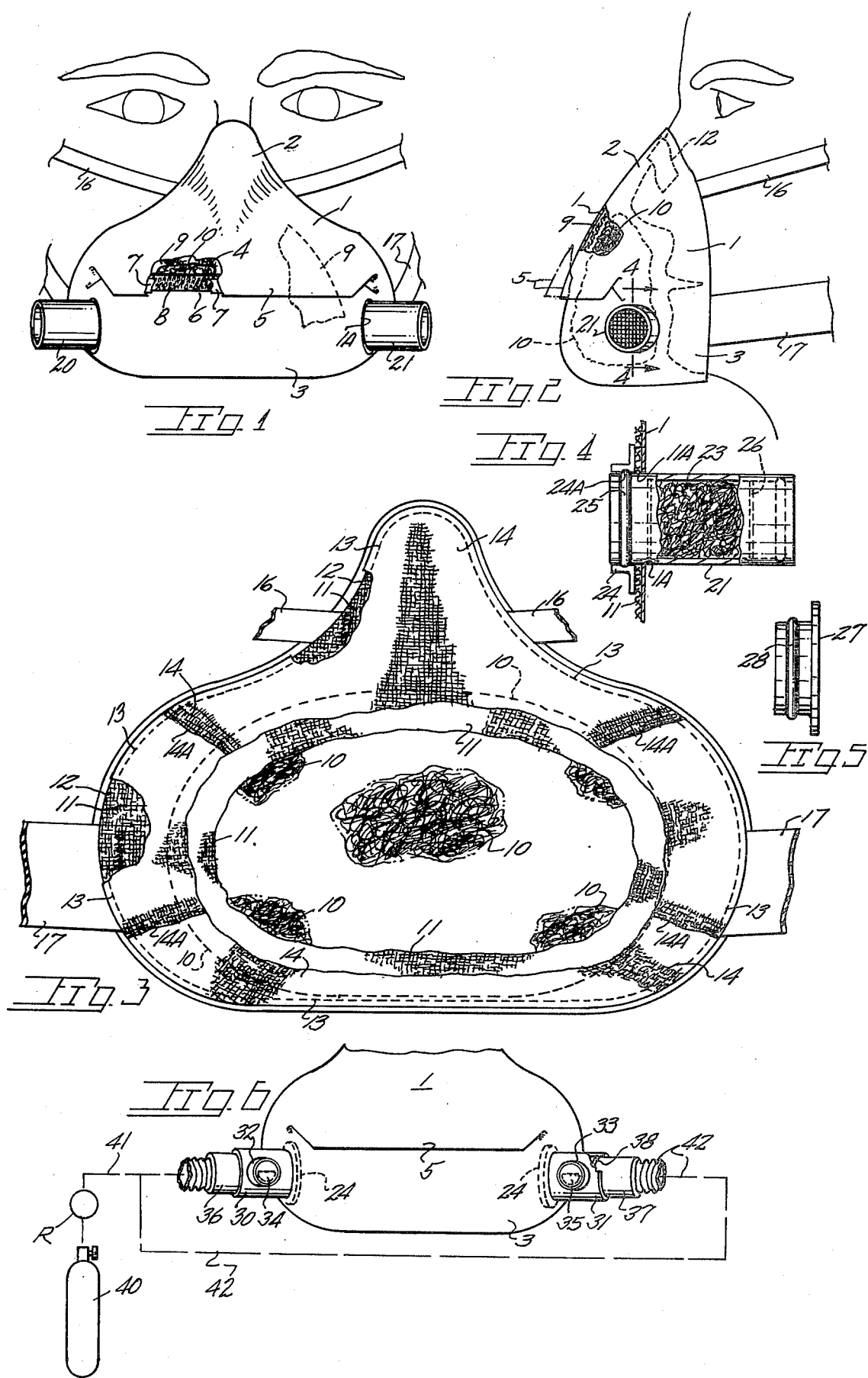

COLD WEATHER RESPIRATORY MASK

BACKGROUND OF THE INVENTION

The present invention is concerned with a mask to be worn over a person's nose and mouth for the purpose of effecting the countercurrent exchange of heat and humidity to diminish body losses of same in severe environments.

The known prior art discloses various types of cold weather face masks which are primarily to protect the face from cold air and which only incidentally provide any pre-heating of inhaled air. For example, U.S. Pat. Nos. 3,768,100 and 4,300,240 disclose cold weather masks where respiration causes intake and exhaust air to pass through a layer of permeable material. U.S. Pat. No. 2,344,920 discloses the objective of routing intake air through receptacles, filled with some type of filtering material, and thence through tubes passing through an internal chamber of the mask to pre-heat the intake air and subsequently mixing said air with exhaled air in a common chamber. Such an arrangement encounters the disadvantage of minimal pre-heating and a sizable chamber into which exhaled air is discharged resulting in a portion of same being re-inhaled by the mask wearer. This reference, while pre-heating fresh air is considered, fails to disclose a mask concept utilizing a countercurrent exchange medium.

U.S. Pat. No. 2,909,782 discloses a cold weather mask wherein breathing results in inhaled and exhaled air passing through a single layer of coarse fabric.

With attention again to U.S. Pat. No. 3,768,100 the same discloses an "oronasal barrier" of air permeable material removably attached to a cold weather mask which has a stated purpose of maintaining inhaled air above ambient temperatures but makes no provision for incorporation of a medium effecting countercurrent exchange.

SUMMARY OF THE PRESENT INVENTION

The present invention is embodied in a mask for wear in temperature severe, arid environments which incorporates a countercurrent exchange medium to substantially reduce the loss of body moisture and heat occurring during respiration.

The publication "SCIENTIFIC AMERICAN" May 1981 issue, Volume 244, No. 5, includes an article entitled "Countercurrent Systems in Animals". Briefly, this disclosure reveals that substantial conservation of body heat and vapor is effected in animals inhabiting severe climates by reason of the countercurrent exchange principle. For example, cold, dry air entering the nasal passages is both heated and humidified by nasal membranes. Conversely, during exhalation the nasal passages serve to recapture a major portion of heat and water vapor. Per the article, the human being is particularly unsuited for benefitting from the countercurrent exchange principle by reason of relatively wide nasal passages and the relatively small surface area of same. Typically, the recovery of heat and moisture is insignificant and of little importance in hospitable environments. In severe cold or warm environments however, considerable body water and heat losses are attributable to respiration.

The present mask incorporates a porous body of material which functions somewhat in the manner of a heat exchanger or sink partaking of both heat and water vapor exhaled by the mask wearer. A reverse flow of inhaled air drawn through the medium conversely is both heated and humidified to drastically reduce the subsequent heating and humidifying tasks of the nasal passages.

The mask fits in a substantially airtight manner about the wearer's nose and chin to minimize dead air space and carbon dioxide buildup. An outer cover or shell is of durable, weather resistant material. An opening in the shell is normally closed by a fabric closure but may be opened for respiratory air passage. Within the shell is located the countercurrent exchange medium which may take several forms. This medium functions as a surface area on which exhaled air may condense thus imparting the heat of vaporization to the medium. Inhaled air drawn into the mask past the medium evaporates the moisture and is heated by the medium thus allowing the user to regain a large proportion of the heat and water vapor normally lost during exhalation. Mask shape results largely from semi-rigid, net-like fabric which permits unimpeded air passage into and out of the nose and mouth of the user. For purposes of comfort a liner is provided intermediate the net-like material and the user's face.

Supplementary countercurrent action may be accomplished by the addition of tubular inserts to the mask each including a quantity of countercurrent medium. Tubular inserts may also serve to provide an interface between the mask and a source of oxygen such as a portable oxygen bottle.

Objectives of the present mask include the provision of a mask for use in severe arid environments which conserves body fluids by providing surfaces on which water vapor may condense for subsequent evaporation by inhaled air for return to the body; the provision of a mask having the capability of conserving body heat by providing a medium acting as a heat sink heated by exhaled air which medium in turn transfers the heat to inhalation air drawn into the mask; the provision of a mask having an air chamber of minimal size to avoid dead air space; the provision of a mask having a removable quantity of countercurrent medium therein highly accessible for convenient replacement; the provision of a mask of compact lightweight construction suitable for use in athletic endeavors by reason of a substantially unrestricted airflow; the provision of a mask adaptable for use with high altitude breathing apparatus; the provision of a mask including an absorbent liner also removably housed within the mask shell.

BRIEF DESCRIPTION OF THE DRAWINGS

In the accompanying drawings:

FIG. 1 is a front elevational view of the mask in place on a wearer's face;

FIG. 2 is a side elevational view of FIG. 1;

FIG. 3 is an enlarged rear elevational view of the present mask with mask components broken away for purposes of illustration;

FIG. 4 is a vertical sectional view taken along line 4—4 of FIG. 2;

FIG. 5 is a side elevational view of a plug removed from a mask opening; and

FIG. 6 is a fragmentary front elevational view of the present mask in combination with an oxygen system shown in schematic form.

DETAILED DESCRIPTION OF THE PREFERRED EMBODIMENTS

With continuing attention to the drawings wherein applied reference numerals indicate components similarly hereinafter identified, the reference numeral 1 indicates a first shell of the mask which overlies the lower portion of the face and includes a nose portion 2 and a chin portion 3.

The shell is of pliable material such as a woven fabric which may be permeable to some extent. Such a material is currently marketed under the registered trademark GORE-TEX. A dual purpose opening in the shell is provided at 4 which is normally concealed by a flap 5 which overlies a shell edge area at 6. The shell, in its normal configuration, is closed by means of fabric closure strips 7 and 8 suitably affixed to the inner side of flap 5 and the outer side of edge area 6. While the shell opening is shown as extending transversely of the shell it may be otherwise formed as, for example, so as to extend upwardly and across the shell nose portion 2 to provide an air opening of greater magnitude than the horizontal opening shown. The opening provides a secondary course for respiratory air as well as enables removal of a later described countercurrent medium.

Immediately rearward or inwardly of the shell is an absorbent insert 9 which serves to collect moisture, if any, forming on the shell interior. Said insert is loosely held in place by the later described components and may be readily removed and replaced via the shell opening. In certain environments the absorbent insert may be dispensed with.

Inwardly of the insert is a mass of a countercurrent medium at 10 formed with a convex outer contour with the opposite side, i.e., the face side, being concave. The mass may be of a non-absorbent fibrous nature such as stainless steel sponge or a mass of synthetic fibres which maintain a given shape while other suitable medium material such as discrete aluminum in minute ball shape may be encapsulated in a net or mesh holder. In a mask for adult use the volume of countercurrent medium used will range between 100-300 cc's.,. The countercurrent medium is removably confined inwardly of the mask shell and exteriorly of a later described shaped member.

Inwardly of shell 1 and medium 10 is a shaped second shell or member 11 which corresponds to the general outline of the shell with a boundary at 12 stitched at 13 to the perimetrical edge area of the shell. Member 11 is suitably formed from semi-stiff net fabric which is highly permeable yet capable of maintaining a concave-convex configuration so as to retain the countercurrent medium in place against the shell interior, or insert 7 if used, and away from the wearer's nose and mouth. The shaped member is preferably non-absorbent and hence may be formed from a synthetic material such as nylon net or other open weave material which lends itself to shaping during mask manufacture. A nose bridge stiffener at 12 is formed from a malleable metal strip and attached to the exterior surface of shaped member 11 to permit shaping of the mask to facial contour.

Stitching 13 also serves to attach a face piece 14 which is coextensive with the shell and shaping member 11. Face piece 14 is of a soft, non-absorbent, highly porous fabric which may loosely adapt to the facial contour to prevent hinderance of jaw movement and air passage to and from the mouth and nose. Folds at 14A permit the face piece to move relative to other mask components during movement of facial features.

Straps at 16 and 17 are stitched at their mask ends to shaping member 11 and extend about the wearer's head respectively above and below the ears to urge the peripheral margin of the mask into lightly biased contact with the nose, cheeks and chin to virtually exclude airflow therepast. Strap adjustment means (not shown) may be integral with the straps.

A supplemental countercurrent medium may be provided by the provision of tubular inserts at 20 and 21 which function as housings for said supplemental medium as typically indicated at 23 within an insert best shown in FIG. 4. A mounting ring at 24 is secured, as by a suitable bonding agent, to the inner side of shaping member 11 which defines an insert receiving opening at 11A. Shell openings are at 1A. An airtight seat may be effected by an insert O-ring at 25 seating within an annular groove 24A within the mounting ring. Barriers at 26 confine the supplemental countercurrent medium.

In FIG. 5, a cap 27 is shown equipped with an O-ring 28 for installation within mounting ring 24 in those instances when supplemental countercurrent exchange is not required.

With attention to FIG. 6, a modified form of mask includes tubular inserts at 30 and 31 each of which is adapted for airtight securement within a mounting ring 24 of the type earlier described. Inserts 30 and 31 may or may not include a quantity of supplemental countercurrent medium. An appendage 32-33 on each tubular insert mounts a flap valve 34-35 which which close in response to reduced internal mask pressure and inward airflow coincident with inhalation and open during exhalation. Hose fittings at 36-37 each includes a seal such as an O-ring at 38 which nests within coupling means on each insert shown as an annular groove formed within the outer end of each insert. A portable source of compressed air or oxygen is at 40 which supplies the mask via a demand type regulator at R and branched hoses at 41-42.

In typical use, for example in a cold arid climate, the mask configuration may dispense with the tubular inserts with the primary countercurrent medium being adequate to conserve body heat and moisture. Respiratory air moves through the open mounting rings 24. Vigorous exercising such as running, downhill skiing, climbing, etc., may result in an accelerated breathing rate of the wearer to the extent it may be desirable to open the mask shell to provide added or secondary airflow beyond that occurring through the ports defined by the mounting rings. Importantly the respiratory airflow is directed away from any eyewear worn by the user. One form of the mask may dispense with the mounting rings and simply rely on the shell opening as a primary route for respiratory air. Should the countercurrent medium become impaired by extreme moisture or frost accumulation, the same may be removed from shell 1 along with absorbent liner insert 7 and an unused quantity of medium inserted into place with or without a new insert 7.

Countercurrent medium 10 may take the form of a lattice network of inert plastic fibres forming a three dimensional mass of material.

In extreme climates the use of the tubular inserts, as shown in FIG. 4, used in pairs, adds additional countercurrent exchange capacity to the mask without unduly hindering the mask wearer. The inserts are of a size to permit convenient carrying of a quantity of same on the person.

While I have shown but a few embodiments of the invention it will be apparent to those skilled in the art that the invention may be embodied still otherwise without departing from the spirit and scope of the invention.

Having thus described the invention, what is desired to be secured under a Letters Patent is:

I claim:

1. A respiratory mask for use in severe arrid environments, said mask comprising, a first shell having nose and jaw portions defining an internal area of the shell of a configuration to cover the wearer's nose and mouth and said first shell defining at least one open area for the passage of respiratory air, retention means for retaining the mask on the user's face, a countercurrent medium positioned within the first shell internal area generally defined by the nose and jaw portions of the first shell and through which inhaled and exhaled respiratory air passes from said at least one open area, said medium having a multitude of air passages along which substantially all respiratory air travels, said medium partaking of the heat from exhaled air and the heat of condensation given up by exhaled water vapor condensing on said medium for subsequent transfer to a reverse flow of respiratory air, a second shell member positioned within the internal area defined by said first shell, said countercurrent medium confined between said first shell and said second shell and said first shell having a flap and defining an opening, said flap overlying and normally closing said opening wherein when the flap is opened, said opening permits insertion and removal of the countercurrent medium as well as providing a secondary course for respiratory air.

2. The respiratory mask claimed in claim 1 wherein said countercurrent medium is a permeable mass of metallic material.

3. The respiratory mask claimed in claim 2 wherein said metallic material is comprised of randomly directed elements and is of concavo-convex shape.

4. The respiratory mask claimed in claim 3 wherein said metallic material is a metal sponge.

5. The respiratory mask claimed in claim 2 wherein said countercurrent medium is of a discrete nature.

6. The respiratory mask claimed in claim 1 wherein said first shell and said second shell substantially correspond in size and shape to one another.

7. The respiratory mask claimed in claim 1 additionally including tubular insert means removably attachable to said second shell.

8. The respiratory mask claimed in claim 7 wherein said insert means includes a quantity of supplemental countercurrent medium.

9. The respiratory mask claimed in claim 8 wherein said insert means additionally includes coupling means adapted to receive a fitting equipped hose for communication with an air supply tank to provide a flow of non-ambient air to the mask.

* * * * *